United States Patent [19]

Winter, III

[11] 4,237,328
[45] Dec. 2, 1980

[54] PROCESS FOR HF-CATALYZED ALKYLATION OF AROMATIC HYDROCARBONS

[75] Inventor: George R. Winter, III, Mt. Prospect, Ill.

[73] Assignee: UOP Inc., Des Plaines, Ill.

[21] Appl. No.: 83,135

[22] Filed: Oct. 9, 1979

[51] Int. Cl.³ .............................................. C07C 2/66
[52] U.S. Cl. .................................. 585/456; 585/464
[58] Field of Search ................................ 585/456, 464

[56] References Cited

U.S. PATENT DOCUMENTS

| 3,275,702 | 9/1966 | Hutson | 585/456 |
| 3,413,373 | 11/1968 | Bloch | 585/450 |
| 3,426,092 | 2/1969 | Carson et al. | 585/302 |
| 3,484,498 | 12/1969 | Berg | 585/450 |
| 3,494,971 | 2/1970 | Fenske | 585/449 |
| 3,501,543 | 3/1970 | Hervert | 585/833 |
| 3,721,720 | 3/1973 | Chapman et al. | 585/723 |
| 3,830,865 | 8/1974 | Anderson | 585/456 |
| 3,950,448 | 4/1976 | Witt | 585/449 |
| 4,072,730 | 2/1978 | Winter | 585/449 |

Primary Examiner—Curtis R. Davis
Attorney, Agent, or Firm—James R. Hoatson, Jr.; John F. Spears, Jr.; William H. Page, II

[57] ABSTRACT

A process for the HF-catalyzed alkylation of aromatic hydrocarbons is disclosed. A liquid-phase alkylation zone effluent stream comprising product alkylaromatic hydrocarbon is passed into an intermediate point of a first fractionation column. A sidecut is removed from the first column at a higher intermediate point and passed into a sidecut stripping column. The bottoms stream of the sidecut stripping column contains the feed aromatic and about 4–10 mole percent paraffinic hydrocarbons and is recycled to the alkylation zone. The overhead vapor stream of the sidecut stripping column is passed into the first column to aid in fractionation.

8 Claims, 1 Drawing Figure

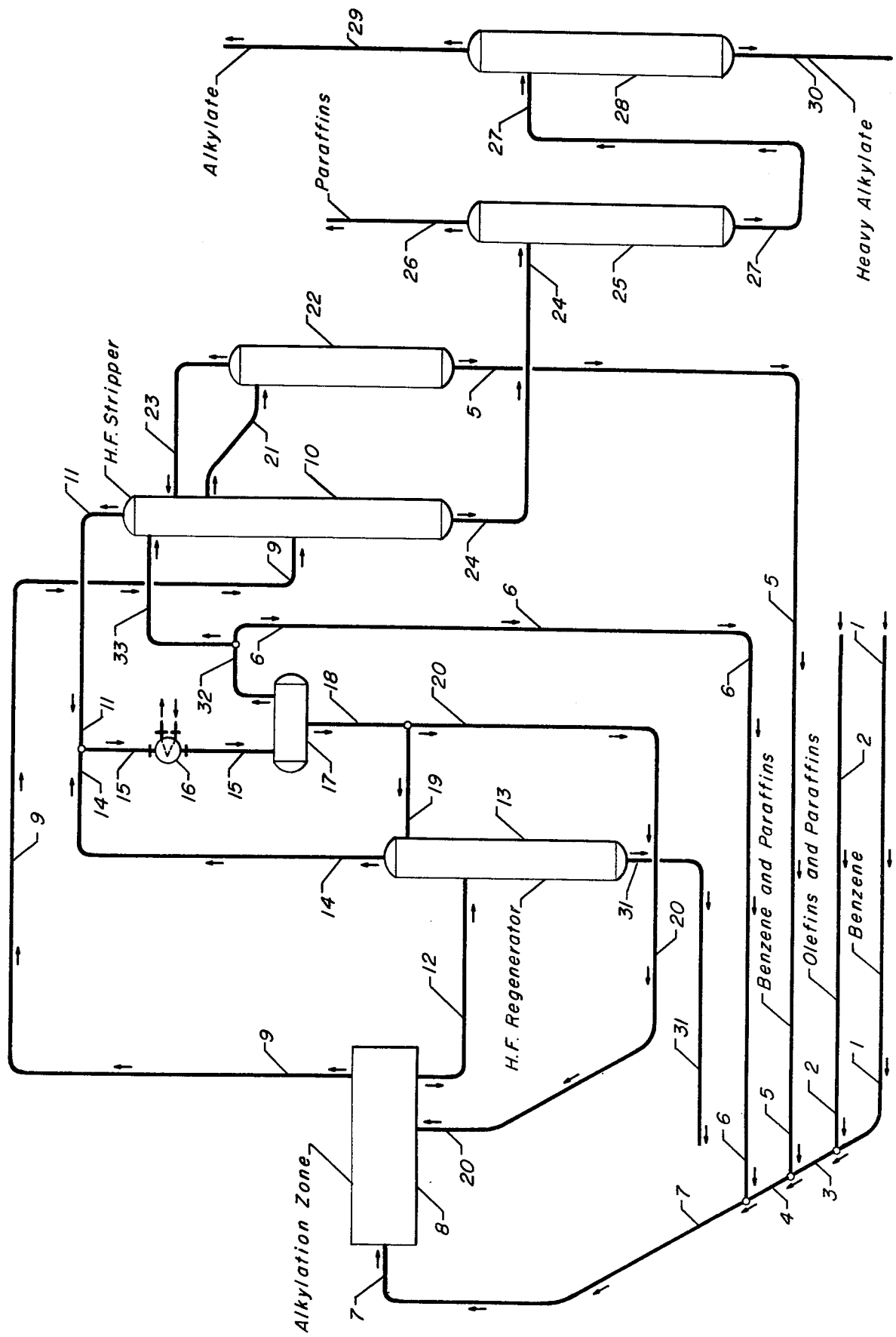

PROCESS FOR HF-CATALYZED ALKYLATION OF AROMATIC HYDROCARBONS

FIELD OF THE INVENTION

The invention relates to a hydrocarbon conversion process such as those often classified in Class 260. The invention more specifically relates to a process for the alkylation of aromatic carbon compounds by the introduction of an acyclic side chain using a catalyst comprising liquid-phase hydrogen fluoride. The invention is directly concerned with a process for the production of linear alkylbenzenes for use in detergent manufacture by the reaction of benzene with a $C_7$–$C_{20}$ monoolefin.

PRIOR ART

The alkylation of aromatic hydrocarbons using hydrogen fluoride as a catalyst is a well established art and is performed commercially on a large scale for the production of detergent grade alkylbenzenes. This process is commonly referred to as detergent alkylation. A representative example of the high state of the art is supplied by U.S. Pat. No. 3,950,448 (Cl. 260-671B). This reference describes the production of a soft detergent alkylate using a two reactor, two settling zone system similar in several respects to that preferred for use in the subject process. The reference also describes the regeneration of the HF used as catalyst and the purification of the products produced by the process.

U.S. Pat. No. 3,950,448 also describes one method for the fractionation of the hydrocarbon phase removed from the alkylation zone. U.S. Pat. No. 3,426,092 (Cl. 260-671) describes a highly similar but more commonly used fractionation method. In both of these references, the paraffins contained in the hydrocarbonaceous effluent of the alkylation zone are concentrated into an overhead stream which is substantially free of other types of hydrocarbons.

U.S. Pat. Nos. 3,275,702 (Cl. 260-671); 3,494,971 (Cl. 260-671); 3,501,543 (Cl. 260-674); 3,501,544 (Cl. 260-674); 3,830,865 (Cl. 260-671R) and 3,484,498 (Cl. 260-671) also describe the production of detergent alkylates.

The passage of the overhead vapor stream of the HF regeneration column and the overhead vapor stream of the HF stripping column into a common single overhead condenser is practiced commercially.

BRIEF SUMMARY OF THE INVENTION

The invention provides an improved process for the HF-catalyzed alkylation of aromatic hydrocarbons. Both the capital and utilities cost of the process are improved. One embodiment of the invention may be broadly characterized as a process for the alkylation of benzene which comprises the steps of admixing liquid-phase benzene, a $C_7$–$C_{20}$ aliphatic monoolefinic hydrocarbon and a normal paraffinic hydrocarbon having the same carbon number as the olefinic hydrocarbon with a first recycle hydrocarbon stream comprising benzene and dissolved HF and a second recycle hydrocarbon stream comprising benzene and the paraffinic hydrocarbon to thereby form an alkylation zone charge stream; contacting the alkylation zone charge stream with liquid-phase HF within an alkylation zone; withdrawing from the alkylation zone a liquid-phase HF stream and a liquid-phase hydrocarbon stream comprising benzene, the paraffinic hydrocarbon, an alkylaromatic hydrocarbon and dissolved HF; passing the liquid-phase hydrocarbon stream into a first fractionation column from which there is removed a first overhead vapor stream comprising HF and benzene and a first bottoms stream comprising the alkylaromatic hydrocarbon and the paraffinic hydrocarbons, with the liquid-phase hydrocarbon stream entering the first fractionation column at a first intermediate point; removing a sidecut liquid stream comprising the benzene and the normal paraffinic hydrocarbon from the first column at a higher second intermediate point, and passing the sidecut stream into a second fractionation column which produces a second overhead vapor stream comprising benzene and a second bottoms stream comprising benzene and containing about 4 mole percent paraffinic hydrocarbons; passing the second overhead vapor stream into the first column at a third intermediate point; admixing the second bottoms stream with feed benzene as the previously specified second recycle hydrocarbon stream; condensing the first overhead vapor stream to produce a hydrocarbon liquid phase, and admixing a stream of this hydrocarbon liquid phase with the feed benzene as the previously specified first recycle hydrocarbon stream; and recovering the product alkylaromatic hydrocarbon from the first bottoms stream.

It is believed that heretofore the overhead vapor stream of the second column, which is normally referred to as the benzene column, has not been passed into the first column. It is also believed that the second column has not been designed and operated to produce a benzene recycle stream which contains a significant amount of paraffinic hydrocarbons. Rather, it is believed that customary practice has been to produce a benzene recycle stream which is substantially free of these hydrocarbons. Furthermore it is believed that heretofore the bottoms stream of the HF stripping column was passed into a column which produced an aromatic hydrocarbon rich overhead stream rather than one rich in paraffinic hydrocarbons.

BRIEF DESCRIPTION OF DRAWING

The Drawing illustrates the preferred embodiment of the invention. For clarity and simplicity, various subsystems and apparatus normally required for the successful operation of the process have not been shown. These items include flow and pressure control valves, heat exchangers, pumps, level control and monitoring systems, etc., which may be of customary design. This representation of the preferred embodiment is not intended to preclude from the scope of the invention those other embodiments set out herein or which are the result of reasonable and normal modification of the inventive concept by those skilled in the art.

Referring now to the Drawing, a stream of liquid phase high purity benzene in line 1 is admixed with a stream comprising a mixture of olefins and paraffins in line 2. The resultant admixture is carried by line 3 to the point at which it is joined by a third liquid stream comprising benzene and paraffins carried by line 5. The material flowing through line 4 is then admixed with a fourth liquid phase stream in line 6 which comprises benzene and dissolved HF. The resultant feed stream is a liquid phase mixture of benzene, olefins and paraffins. It is passed into an alkylation zone 8 through line 7. Also passed into the alkylation zone is a stream of liquid-phase HF carried by line 20.

Two effluent streams are removed from the alkylation zone 8. These effluent streams are the result of the phase separation in this zone of the HF and the hydrocarbons. The denser HF phase is removed through line 12 and passed into a fractionation column 13 utilized as an HF regenerator. A small stream of reaction by-products is removed from the HF regenerator through line 31. The overhead vapor stream removed from the HF regenerator in line 14 comprises vapor phase HF and any relatively volatile hydrocarbons which are dissolved in the liquid phase HF flowing through line 12. The overhead vapor stream of the HF regenerator is admixed with a second overhead vapor stream from line 11 and passed through an overhead condenser 16 via line 15. The resultant condensate is passed into an overhead receiver 17 and therein separated into a less dense hydrocarbon phase and an HF phase. The HF phase is withdrawn through line 18 and divided into a first portion which is returned to the HF regenerator through line 19 as reflux and a second portion which is passed into the alkylation zone 8 through line 20. The hydrocarbon phase is rich in benzene and contains a small amount of dissolved HF. The hydrocarbon phase is removed through line 32. A first portion of the hydrocarbon phase is passed into column 10 as reflux. A second portion is passed into the alkylation zone 8 through line 6.

A stream of liquid phase hydrocarbons comprising benzene, paraffins and the product detergent alkylate is removed from the alkylation zone 8 through line 9 and passed into a fractionation column 10 referred to herein as the HF stripper. The HF stripper is operated at conditions effective to separate the entering material into a bottoms stream removed through line 24 which comprises the product detergent alkylate and paraffins and an overhead vapor stream removed through line 11 which comprises benzene and the HF which was dissolved in the liquid flowing through lines 9 and 33. The overhead vapor stream of the HF stripper is admixed with the overhead vapor stream of the HF regenerator and processed as described above.

The bottoms stream of the HF stripper is substantially free of benzene and is passed into a third fractionation column 25 normally referred to as the paraffin column. This third column is operated at conditions effective to separate the entering hydrocarbons into a net overhead product stream having a high paraffin concentration which is removed through line 26 and a net bottoms stream removed through line 27. The net bottoms stream of the third column is passed into a fourth fractionation column 28. The fourth fractionation column is operated at conditions effective to separate the entering hydrocarbon mixture into a net overhead product stream of the product detergent alkylate removed in line 29 and a smaller net bottoms stream of heavy alkylate removed in line 30.

A sidecut stream is removed from the HF stripper 10 through line 21 and passed into the upper portion of fractionation column 22. This fractionation column is operated as a sidecut stripper under conditions effective to reject all HF entering the column as part of the overhead vapor removed through line 23. The overhead vapor of the sidecut stripper comprises a mixture of HF, benzene and paraffins and is passed into the HF stripper at an upper intermediate point which allows the utilization of the heat content of the overhead vapor stream within the HF stripper. A net bottoms stream is removed from the sidecut stripper through line 5. This bottoms stream is substantially free of HF and contains a mixture of benzene and paraffins.

DETAILED DESCRIPTION

One of the more important HF acid catalyzed alkylation reactions is the production of detergent grade alkylated aromatic hydrocarbons. This "detergent alkylate" is formed by the reaction of benzene with an olefinic hydrocarbon having from seven to twenty carbon atoms per molecule. A better quality detergent precursor normally results from the use of olefinic hydrocarbons having from about ten to fifteen carbon atoms per molecule.

The detergents produced from the resulting alkylated aromatic hydrocarbons are classified either as "soft" if they meet certain standards of biodegradability or as "hard" if they are relatively nonbiodegradable. Soft detergents are the result of using a long-chain monoolefin as the olefinic reactant. The preferred method of producing these olefins is by the dehydrogenation of the corresponding normal paraffins. The dehydrogenation zone may be integrated with the detergent alkylation process as described in U.S. Pat. Nos. 3,413,373; 3,484,498 and 3,494,971. Hard detergents result from the use of branched chain olefins such as propylene tetramer produced in a catalytic condensation process. The use of soft detergents is becoming more widespread, and the subject invention will therefore be discussed primarily in terms of soft detergent production.

It is the objective of this invention to provide a process for the HF-catalyzed production of alkylated aromatic hydrocarbons. It is a further objective to provide an improved process for the production of linear alkylbenzenes suitable for use in the production of detergents. It is a specific objective to reduce the capital and utilities cost of an HF-catalyzed process for the production of detergent alkylate.

The aromatic hydrocarbon which is alkylated in the subject process is preferably benzene, but may be a higher molecular weight aromatic hydrocarbon. The feed aromatic hydrocarbon may therefore be toluene, a xylene, ethylbenzene, phenol, naphthalene, etc. The olefinic hydrocarbon which is consumed in the production of detergent alkylate may have from about 6–20 carbon atoms per molecule. A better quality detergent precursor normally results from the use of linear olefinic hydrocarbons having from 10–15 carbon atoms per molecule. When these olefinic hydrocarbons are produced in a dehydrogenation process which is integrated with the alkylation process, it is common practice to pass the unseparated paraffin/olefin mixture produced as the effluent of dehydrogenation process into the alkylation process as the olefin-containing feed stream. This is basically because of the high cost of separating olefins and paraffins of the same carbon number. The olefin-containing feed stream charged to the alkylation process may therefore contain from about 30 to about 70 mol.% of paraffins having the same number of carbon atoms per molecule as the olefinic hydrocarbons. These relatively non-reactive paraffins pass through the alkylation process in the various hydrocarbon phase streams and are eventually separated from the alkylate by fractionation and then charged to the dehydrogenation process.

As used herein, the term "alkylation zone" is intended to indicate the process equipment in which the aromatic hydrocarbon and the olefin are reacted and in which subsequent contacting, treating and phase separation steps are performed upstream of the passage of an alkylate-containing hydrocarbon stream into a fractionation zone. The preferred configuration of the alkylation zone comprises a first reaction zone, a first phase separation zone, a second reaction (contacting) zone and a second phase separation zone. Preferably, the reactants and recirculated HF are charged to the first reaction zone and a single effluent stream comprising the admixed HF and hydrocarbons is passed from the first reaction zone to the first settling zone. A hydrocarbon phase which forms in the first settling zone is then passed into the second reaction zone in admixture with newly regenerated HF. The total effluent of the second reaction zone is then passed into the second separation zone. The hydrocarbon phase which forms in the second separation zone is passed into the HF stripping column. Other alkylation zone flow schemes and arrangements may also be used in conjunction with the inventive concept.

Chemical reactions which involve olefinic hydrocarbons and which are catalyzed by hydrogen fluoride usually proceed at a very fast rate. To reduce the amount of olefin polymerization and to promote the production of a mono-alkylated aromatic product, the reactants are normally subjected to vigorous mixing and agitation at the point of initial contact of the olefinic hydrocarbons and the liquid-phase hydrogen fluoride. The desired result is a uniform dispersion and intimate contacting of the hydrocarbon and hydrogen fluoride phases and the avoidance of localized high temperatures or localized high concentrations of either the olefinic hydrocarbon or the hydrogen fluoride. The initial contacting of the reactants and the catalyst has been done in a number of different ways. For instance, the olefinic hydrocarbons have been sprayed into a mixture of hydrogen fluoride and hydrocarbons through nozzles, and mixtures of the reactants have been released into eductors as high velocity streams which cause the eduction and admixture of the hydrogen fluoride. U.S. Pat. No. 4,134,734 describes a unitary reactor for the production of detergent alkylate. U.S. Pat. No. 4,072,730 describes a process for producing detergent alkylate in which a centrifugal pump is utilized as the first reaction zone due to the intense agitation which occurs within the pump.

The reaction zone is maintained at alkylation-promoting conditions. As used herein, the term "alkylation-promoting conditions" is intended to include a pressure sufficient to maintain the reactants and HF in a liquid phase. A general range of operating pressures is from about 2 to 41 atmospheres absolute. The temperature range covered by this set of conditions is from about $-20°$ C. to about 95° C., but the reaction is preferably conducted at a temperature of from 15° C. to 50° C. The volumetric ratio of HF to the total amount of hydrocarbons entering the first reaction zone should be maintained within the broad range of from about 0.2:1.0 to about 10:1. A preferred range for this ratio is from 1.0:1.0 to 2.5:1.0. To lessen the production of polyalkylated benzenes and to reduce the amount of olefin polymerization in the first reaction zone, the mole ratio of benzene to the monoolefin at the point of initial olefin-acid contact is maintained above 1.0:1.0, but preferably below 10.0:1.0. A range of typical commercial ratios is from 3.0:1.0 to about 8.0:1.0.

The conditions maintained within the contacting zone, which is referred to as the second reaction zone in most prior art references, are similar to these alkylation-promoting conditions, but some adjustment is required. For instance, since essentially all of the olefin has been consumed in the first reaction zone, the hydrocarbon stream fed to the contacting zone is substantially free of olefins. There is therefore no benzene to olefin ratio to be specified. The same pressure range may be used in the contacting zone as in the reaction zone, but a higher temperature is preferred. This higher temperature should be at least 6 to 10 Centigrade degrees above that used in the reaction zone. All temperatures specified herein are intended to refer to the average temperature of the liquid stream entering the respective zone.

The acid-hydrocarbon ratio maintained in the contacting zone will normally be slightly lower, and a typical ratio is about 1:1. The purity of acid used in the contacting zone will, however, be higher. This is preferred because of the greater effectiveness of higher purity acid for the treatment of the alkylate. This treatment consists of the defluorination of the alkylate product and the extraction of naphthalenes and anthracenes. A higher acid purity is obtained by admixing the newly regenerated acid into the alkylate-containing hydrocarbon stream entering the contacting zone. The recycle acid used in the reaction zone is withdrawn from the second settling zone and therefore contains a higher concentration of high molecular weight hydrocarbonaceous impurities. The acid used in the reaction and contacting zones may be from about 85–92 wt.% HF and will typically be about 90 wt.% HF. The acid used in the third reaction zone preferably contains more than 90 wt.% HF and is typically about 93–94 wt.% HF.

The effluent streams leaving the reaction zone and the contacting zone will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into settling zones.

The two settling zones will normally be maintained at a temperature which is set by the entering HF-hydrocarbon mixtures withdrawn from the respective upstream zones. They will therefore be at substantially the same temperature as the immediately upstream reaction or contacting zone. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 10 minutes but less than 30 minutes.

Those skilled in the art are familiar with the regeneration of the HF acid catalysts. Information about the apparatus and conditions utilized for this operation is contained in the previously cited patents and also in U.S. Pat. No. 3,721,720. The regeneration operation is often accomplished by stripping the acid under conditions sufficient to decompose alkylfluorides and to produce an overhead vapor stream containing HF and a small amount of vapor phase hydrocarbons. If desired, a stripping media comprising a relatively volatile hydrocarbon may be charged to the bottom of the HF regeneration column. Benzene available within the process is a suitable stripping media. Use of a stripping media is optional and reduces the temperature required at the bottom of the HF regeneration column. The HF regeneration column may be refluxed with liquid-phase HF or with liquid-phase aromatic hydrocarbons.

The liquid-phase hydrocarbon stream which contains the product alkylate and which is withdrawn from the alkylation zone is passed into a fractionation column referred to herein as the HF stripping column and as the HF stripper. This is in accordance with the customary nomenclature used in describing the various components of an HF-catalyzed detergent alkylation process.

In the practice of the subject invention, the liquid-phase hydrocarbon stream withdrawn from the alkylation zone is passed into the HF stripping column at an intermediate point. As used herein, the term "intermediate point" and similar terms is intended to indicate a point in the fractionation column which is separated from each end of the column by at least three fractionation trays. It has been customary to feed this stream into the top of the HF stripping column. It also has been customary to pass the net bottoms stream of the HF stripping column into a second column referred to as the benzene column when benzene is consumed in the process. Substantially all the unreacted benzene was concentrated into the overhead stream of this column and then recycled to the alkylation zone.

In the subject process, the net bottoms stream of the HF stripping column is passed into the column which in the normal fractionation sequence is referred to as the paraffin column. This is possible because, unlike the prior art process flows, the bottoms stream of the HF stripping column is free of benzene or any other feed aromatic hydrocarbon. The total absence of benzene may not be possible. However this stream should be substantially free of benzene, which is intended to indicate an aromatic hydrocarbon concentration of less than 0.5 mole %. Representative conditions for the operation of the HF stripping column include an overhead vapor temperature of about 250° F. at a pressure of approximately 36 psig. In the prior art processes, there is normally no external reflux to this column. However, in the subject process, reflux is supplied from the overhead receiver. The overhead vapor stream of the HF stripping column is normally condensed by cooling it to about 100° F. or less.

A sidecut stream is removed from the HF stripping column at an intermediate point above the feed point of the column. The number of trays separating the feed point and this upper second intermediate point should be sufficient to insure that the liquid present at this point in the column has a very low concentration of the product alkylate. This sidecut stream is passed into the top of a sidecut stripper column which functions as the benzene column in the subject process. The overhead vapor stream of this column is passed into the HF stripping column at a third intermediate point which is above the feed point of the HF stripping column. Preferably, the third intermediate point is above the second intermediate point. The bottoms stream of the sidecut column will contain at least 4.0 mole percent paraffins. The paraffin concentration in this stream is preferably between 5 and 10 mole percent, but higher concentrations may be also maintained in this stream.

The net bottoms stream of the HF stripping column is passed into a fractionation zone in which the product alkylate is recovered. Preferably, this zone contains a third fractionation column referred to as a paraffin column. Non-reactive paraffins are removed from this column as an overhead liquid stream. The bottoms stream of the third fractionation column comprises the product alkylate and any higher molecular weight hydrocarbons formed by side reactions. This bottoms stream is passed into a fourth fractionation column which produces a high purity net overhead stream containing the detergent alkylate which is removed as a product stream. A bottoms stream comprising polymerized olefins and polyalkylated benzenes (heavy alkylate) is removed for disposal. The third and the fourth fractionation columns are normally operated at a subatmospheric pressure. An alternative method of performing this separation is disclosed in U.S. Pat. No. 3,950,448.

One embodiment of the invention may be characterized as a process for the alkylation of aromatic hydrocarbons which comprises the steps of forming an alkylation zone charge mixture by admixing a liquid-phase hydrocarbon feed stream comprising an aromatic hydrocarbon, an aliphatic monoolefinic hydrocarbon having from about 7 to 20 carbon atoms per molecule and a normal paraffinic hydrocarbon having the same number of carbon atoms per molecule as the monoolefinic hydrocarbon, a first recycle hydrocarbon stream comprising the aromatic hydrocarbon and dissolved HF, and a second recycle hydrocarbon stream comprising the aromatic hydrocarbon and the normal paraffinic hydrocarbon; contacting the alkylation zone charge stream with liquid-phase HF within an alkylation zone maintained at alkylation-promoting conditions; withdrawing from the alkylation zone a liquid-phase HF stream and a liquid-phase hydrocarbon stream comprising the aromatic hydrocarbon, the normal paraffinic hydrocarbon, an alkylaromatic hydrocarbon and dissolved HF; passing the liquid-phase hydrocarbon stream into a first fractionation column from which there is removed a first overhead vapor stream comprising HF and the aromatic hydrocarbon and a first bottoms stream comprising the alkylaromatic hydrocarbon and the normal paraffinic hydrocarbon, with the liquid-phase hydrocarbon stream entering the first fractionation column at a first intermediate point; removing a sidecut liquid stream comprising the aromatic hydrocarbon and the normal paraffinic hydrocarbon from the first fractionation column at a higher second intermediate point, and passing the sidecut liquid stream into a second fractionation column operated at conditions effective to produce a second overhead vapor stream which comprises the aromatic hydrocarbon and a second bottoms stream which comprises the aromatic hydrocarbon and which has a normal paraffinic hydrocarbon concentration above about 4 mole percent; passing the second overhead vapor stream into the first fractionation column at a third intermediate point which is above the second intermediate point; admixing the second bottoms stream with the liquid-phase hydrocarbon feed stream as the second recycle hydrocarbon stream; condensing the first overhead vapor stream to produce a hydrocarbon liquid phase, and admixing a stream of the hydrocarbon liquid phase with the liquid-phase hydrocarbon feed stream as the first recycle hydrocarbon stream; and passing the first bottoms stream into a fractionation zone in which the product alkylaromatic hydrocarbon is recovered.

The presence of paraffinic hydrocarbons in the bottoms stream of the sidecut stripper is both unique and beneficial. Since it is not attempted to totally reject these hydrocarbons from the top of the column, the separation is relatively easy and the energy consumption is relatively low. The sidecut stripper will therefore require fewer fractionation trays and will be less costly.

The paraffins in the bottoms stream pass through the alkylation substantially uneffected and may be considered as additional diluent. There is an improvement over prior art processes in that the latent heat content of the overhead vapor stream of the sidecut stripper is utilized within the process. This heat and some sensible heat aids in the fractionation performed in the upper portion of the HF stripping column. It is therefore not immediately rejected as low level heat in the overhead condenser. This should reduce the utilities cost of operating the columns. In addition, the overhead condenser which receives the vapors of the prior art benzene column is no longer required. Only one overhead condenser is required for three columns. This lowers both the required equipment and the utilities cost of condensing the overhead vapors as compared to the prior art. The capital cost and the operating cost of the alkylation process are therefore reduced.

I claim as my invention:

1. In a process for the production of linear alkylaromatic hydrocarbons which comprises the steps of:
    (a) contacting a liquid-phase hydrocarbon mixture comprising benzene, and aliphatic monoolefinic hydrocarbon having from about 7 to 20 carbon atoms per molecule and a normal paraffinic hydrocarbon having the same number of carbon atoms per molecule as the aliphatic monoolefinic hydrocarbon with liquid-phase HF within an alkylation zone maintained at alkylation-promoting conditions;
    (b) withdrawing from the alkylation zone a liquid-phase hydrocarbon stream comprising benzene, the normal paraffinic hydrocarbon, an alkylaromatic hydrocarbon and dissolved HF;
    (c) passing the liquid-phase hydrocarbon stream into a first fractionation column from which there is removed a first overhead vapor stream comprising HF and benzene and a first bottoms stream comprising the alkylaromatic hydrocarbon and the normal paraffinic hydrocarbon; the improvement which comprises:
        (i) passing the liquid-phase hydrocarbon stream into the first fractionation column at a first intermediate point;
        (ii) removing a sidecut liquid stream comprising benzene, HF, and the normal paraffinic hydrocarbon from the first fractionation column at a higher second intermediate point and passing the sidecut liquid stream into a second fractionation column operated at conditions effective to produce a second overhead vapor stream which comprises benzene and HF and a second bottoms stream which comprises benzene and which has a normal paraffinic hydrocarbon concentration above 4.0 mole percent;
        (iii) passing the second overhead vapor stream into the first fractionation column at a third intermediate point;
        (iv) passing the second bottoms stream into the alkylation zone; and,
        (v) passing the first bottoms stream into a fractionation zone in which the product alkylaromatic hydrocarbon is recovered.

2. The improvement of claim 1 further characterized in that the concentration of the normal paraffinic hydrocarbon in the second bottoms stream is between 5.0 and about 10.0 mole percent.

3. A process for the alkylation of aromatic hydrocarbons which comprises the steps of:
    (a) forming an alkylation zone charge liquid by admixing a liquid-phase hydrocarbon feed stream comprising an aromatic hydrocarbon, an aliphatic monoolefinic hydrocarbon having from about 7 to 20 carbon atoms per molecule and a normal paraffinic hydrocarbon having the same number of carbon atoms per molecule as the monoolefinic hydrocarbon, a first recycle hydrocarbon stream comprising the aromatic hydrocarbon and dissolved HF, and a second recycle hydrocarbon stream comprising the aromatic hydrocarbon and the normal paraffinic hydrocarbon;
    (b) contacting the alkylation zone charge liquid with liquid-phase HF within an alkylation zone maintained at alkylation-promoting conditions;
    (c) withdrawing from the alkylation zone a liquid-phase HF stream and a liquid-phase hydrocarbon stream comprising the aromatic hydrocarbon, the normal paraffinic hydrocarbon, an alkylaromatic hydrocarbon and dissolved HF;
    (d) passing the liquid-phase hydrocarbon stream into a first fractionation column from which there is removed a first overhead vapor stream comprising HF and the aromatic hydrocarbon and a first bottoms stream comprising the alkylaromatic hydrocarbon and the normal paraffinic hydrocarbon, with the liquid-phase hydrocarbon stream entering the first fractionation column at a first intermediate point;
    (e) removing a sidecut liquid stream comprising the aromatic hydrocarbon and the normal paraffinic hydrocarbon from the first fractionation column at a higher second intermediate point, and passing the sidecut liquid stream into a second fractionation column operated at conditions effective to produce a second overhead vapor stream which comprises the aromatic hydrocarbon and a second bottoms stream which comprises the aromatic hydrocarbon and which has a normal paraffinic hydrocarbon concentration above about 4 mole percent;
    (f) passing the second overhead vapor stream into the first fractionation column at a third intermediate point;
    (g) admixing the second bottoms stream with the liquid-phase hydrocarbon feed stream as the second recycle hydrocarbon stream of step (a);
    (h) condensing the first overhead vapor stream to produce a hydrocarbon liquid phase, and admixing a stream of the hydrocarbon liquid phase with the liquid-phase hydrocarbon feed stream as the first recycle hydrocarbon stream of step (a); and,
    (i) passing the first bottoms stream into a fractionation zone in which the product alkylaromatic hydrocarbon is recovered.

4. The process of claim 3 further characterized in that the concentration of the normal paraffinic hydrocarbon in the second bottoms stream is between 5.0 and about 10.0 mole percent.

5. The process of claim 4 further characterized in that the first bottoms stream is substantially free of the aromatic hydrocarbon.

6. The process of claim 5 further characterized in that the third intermediate point is above the second intermediate point.

7. The process of claim 6 further characterized in that the aromatic hydrocarbon is benzene.

8. The process of claim 7 further characterized in that the aliphatic monoolefinic hydrocarbon has from 10 to 15 carbon atoms per molecule.

* * * * *